United States Patent
Phillips et al.

(10) Patent No.: US 7,389,710 B2
(45) Date of Patent: Jun. 24, 2008

(54) SWIVEL RETRACTOR BLADE ASSEMBLY

(75) Inventors: Burns P. Phillips, Nashville, TN (US); Larry Griffith, Lakeville, MN (US)

(73) Assignee: Boss Instruments, Ltd., Inc., Earlysville, VA (US)

( * ) Notice: Subject to any disclaimer, the term of this patent is extended or adjusted under 35 U.S.C. 154(b) by 0 days.

(21) Appl. No.: 11/633,801

(22) Filed: Dec. 5, 2006

(65) Prior Publication Data

US 2007/0142712 A1 Jun. 21, 2007

Related U.S. Application Data

(63) Continuation of application No. 10/687,267, filed on Oct. 15, 2003, now Pat. No. 7,191,683.

(60) Provisional application No. 60/418,774, filed on Oct. 15, 2002.

(51) Int. Cl.
G05G 1/04 (2006.01)
(52) U.S. Cl. .................................... 74/577 M
(58) Field of Classification Search .......... 74/575, 74/577 R, 577 S, 577 M; 600/215, 227, 228, 600/229, 230
See application file for complete search history.

(56) References Cited

U.S. PATENT DOCUMENTS

| 497,064 | A | 5/1893 | VanMeter |
| 569,839 | A | 10/1896 | Rocloffs |
| 1,018,868 | A | 2/1912 | Breneman |
| 1,500,227 | A | 7/1924 | Breneman |
| 1,727,879 | A | 9/1929 | Hodlick et al. |
| 2,623,517 | A | 12/1952 | Barlow et al. |
| 2,670,732 | A | 3/1954 | Nelson |
| 3,965,890 | A | 6/1976 | Gauthier |
| 4,010,741 | A | 3/1977 | Gauthier |
| 4,143,652 | A | 3/1979 | Meier et al. |
| 4,421,108 | A | 12/1983 | Cabrera et al. |
| 4,616,635 | A | 10/1986 | Caspar et al. |
| 4,813,401 | A | 3/1989 | Grieshaber |
| 4,971,038 | A | 11/1990 | Farley |
| 5,375,481 | A | 12/1994 | Cabrera et al. |
| 5,882,298 | A | 3/1999 | Sharratt |
| 5,902,233 | A | 5/1999 | Farley et al. |
| 5,931,777 | A | 8/1999 | Sava |
| 5,993,385 | A | 11/1999 | Johnston et al. |
| D420,130 | S | 2/2000 | Nicholas et al. |
| 6,042,540 | A | 3/2000 | Johnston et al. |
| 6,196,969 | B1 | 3/2001 | Bester et al. |
| 6,241,659 | B1 | 6/2001 | Bookwalter et al. |
| 6,340,345 | B1 | 1/2002 | Lees et al. |

(Continued)

Primary Examiner—Vicky A Johnson
(74) Attorney, Agent, or Firm—McDermott Will & Emery LLP

(57) ABSTRACT

A retractor clamp assembly includes a clamp positionable about a support ring. A retractor shaft extends from the clamp and has a connector at the end with a retractor blade connected thereto by a stem. The connector is preferably equipped with a first slot limiting the side to side angular range of motion of the retractor blade stem relative to the retractor shaft, and a second slot limiting the top to bottom range of motion of the retractor blade stem relative to the retractor shaft. This allows the retractor blade to be maintained and/or positioned in an optimum position relative to retracted tissue while allowing the retractor shaft to be selectively positioned by a user.

9 Claims, 2 Drawing Sheets

U.S. PATENT DOCUMENTS

| | | |
|---|---|---|
| D453,377 S | 2/2002 | Schollhorn et al. |
| 6,431,025 B1 | 8/2002 | Koros et al. |
| 6,572,540 B2 | 6/2003 | Dobrovolny |
| 6,602,190 B2 | 8/2003 | Dobrovolny |
| 6,620,097 B1 | 9/2003 | Bookwalter et al. |
| 6,663,562 B2 | 12/2003 | Chang |
| 6,729,205 B2 | 5/2004 | Phillips |

SWIVEL RETRACTOR BLADE ASSEMBLY

CLAIM OF PRIORITY

This application is a continuation of U.S. application Ser. No. 10/687,267, filed Oct. 15, 2003 now U.S. Pat. No. 7,191,683, which application claims the benefit of U.S. Provisional Application No. 60/418,774 filed Oct. 15, 2002, both of which are incorporated herein by reference and made a part hereof.

FIELD OF INVENTION

The present invention relates to a retractor blade which is adjustably connected to a retractor shaft, and more particularly to a retractor blade connected to a retractor shaft with a ball socket connection allowing free movement while limiting the range of motion of the retractor blade relative to the retractor shaft.

DETAILED DESCRIPTION OF RELATED ART

Co-pending and co-owned patent application Ser. No. 10/113,663 shows a multi-position ratchet mechanism for connecting a retractor blade to a ring, which is incorporated by reference. The 10/113,663 application is not prior art, but the development of the technology disclosed in that application assisted the applicant in determining that a need existed for the invention disclosed herein.

The new clamp allows for a retractor blade to be connected by a retractor shaft to the clamp when the clamp is connected to a ring, when the clamp is pivoted downwardly into the wound or from left to right relative to the ring, a fixably mounted retractor blade connected to the retractor shaft as has been traditionally done in the prior art and shown in U.S. Pat. No. 4,354,763, does not maintain the retractor blade in a substantially perpendicular alignment relative to the direction of retraction. The retractor blade is most effective when the majority of the surface area is against tissue (i.e., perpendicular to the direction of retraction) so that proper retraction can occur.

Accordingly, with the development of the multi-positioning clamp as described in U.S. patent application Ser. No. 10/113,663, a need has arisen for improved connection intermediate the retractor blade and the retractor shaft so that the intimate contact with the retractor blade against the tissue may be maintained in spite of the angular relationship of the retractor shaft relative to the multi-position ratchet mechanism, or other angularly adjustable clamp.

SUMMARY OF THE INVENTION

A need exists for an improved connector intermediate a retractor blade and retractor shaft so that an optimal amount of retractor blade may be maintained against tissue in spite of the angular position of the retractor shaft relative to a clamp connecting the retractor shaft to a ring.

A need also exists for an improved retractor blade assembly which is free to rotate to an optimal retraction position when the retractor shaft is not necessarily oriented along a vector oriented in the direction of retraction.

Another need exists for the ability to maintain the retractor blade perpendicular to the direction of retraction when the retractor shaft is not optimally oriented for such retraction.

Accordingly, a retractor assembly is comprised of a retractor blade connected by a stem to a connector and the retractor shaft. The retractor shaft is preferably connected to a ring, which is not necessarily circular, by a rotatable and/or pivoting clamp. The connector allows for the self adjustability of the angle of the retractor blade relative to the retractor shaft as the angle of the retractor shaft relative to the ring is adjusted at the clamp. The connector is preferably a pivoting type connector, but others could also be employed.

Since rings are typically located proximate an elevation of the incision, in the preferred embodiment a limited travel is allowed in the up and down direction. The side to side, or lateral travel, of the retractor shaft relative to the stem connected to the retractor blade in the preferred embodiment is about 120° range of motion so the connector allows for the pivoting of the retractor blade relative to the retractor shaft sufficient to account for an offset of the retractor blade relative to the ring in the direction of the retraction.

It is preferred that the type connection connect the retractor blade to the retractor shaft while allowing the desired range of motion of the ball retractor blade relative to the retractor shaft.

BRIEF DESCRIPTION OF THE DRAWINGS

The particular features and advantages of the invention as well as other objects will become apparent from the following description taken in connection with the accompanying drawings in which.

DETAILED DESCRIPTION OF THE PREFERRED EMBODIMENT

Figure 1:
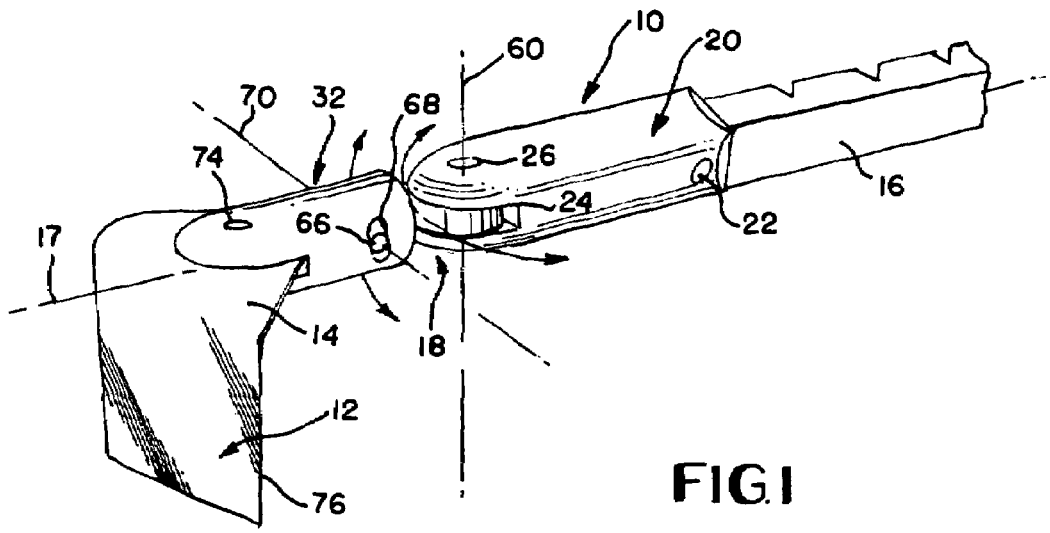
FIG. 1 is a top perspective view of a retractor blade assembly having a retractor blade connected to a retractor shaft with a connector in accordance with the preferred embodiment of the present invention.
Figure 2:
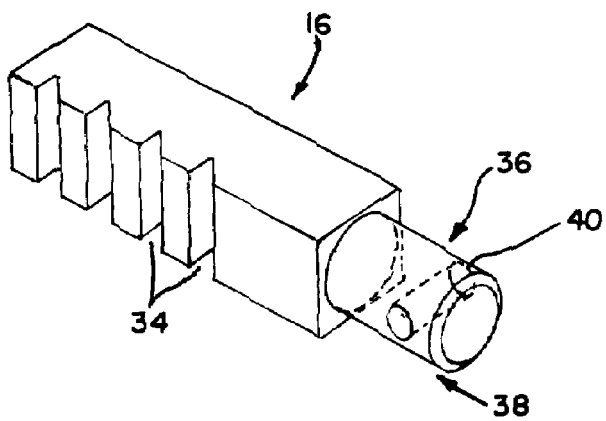
FIG. 2 is a side perspective view of the shaft portion of the retractor blade assembly shown in FIG. 1.

Accordingly, FIG. 1 shows an assembly 10 of the preferred embodiment. The assembly 10 is comprised of a retractor blade 12 having a stem or shoulder 14. The assembly 10 also has a retractor shaft 16. The retractor shaft 16 and the retractor blade 12 are joined at connector 18 which is preferably a pivoting type connection. Other connectors like a ball and socket type connection could also be utilized.

Figure 6:
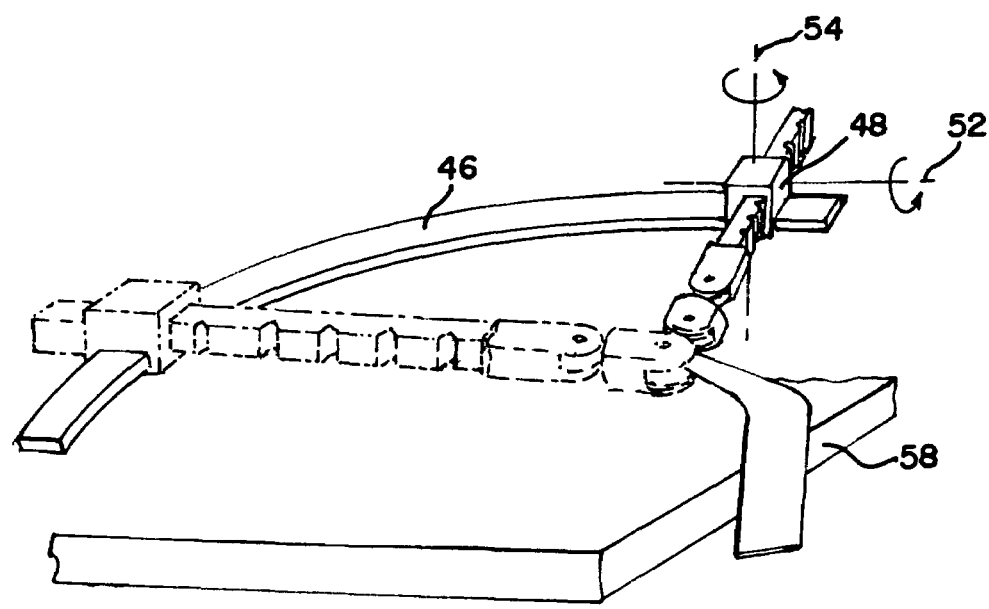
FIG. 6 is a practical application of the use of the retractor blade in conjunction with the retractor shaft and connected in accordance with the present invention with one location option shown in phantom.

A description of the component parts is helpful to understand the anticipated positioning in order to show the capabilities of the assembly 10 shown in FIG. 1 and FIG. 6. The retractor shaft 16 is preferably equipped with a plurality of angled cuts 34 which allow for a clamp 48 as shown in FIG. 6 to ratchetly or otherwise retain the retractor shaft 16 at a desired position relative to a ring 46 or other appropriate structure. The shaft 16 preferably has a substantially square cross section along a majority of its length with a connection 36 at a distal end 38.

The pivoting connection is preferably constructed having a flange clevis 20 which connects to the retractor shaft 16 with a pin 22. The flange clevis 20 connects to a pivot flange 24 which pivots about pin 26 as shown in FIG. 1. Preferably the flange clevis 20 can pivot at least 60 degrees, if not 90 degrees to either side of shaft axis 17. In other embodiments, ranges of +/−30 degrees or +/−45 degrees may also be utilized.

Figure 4:
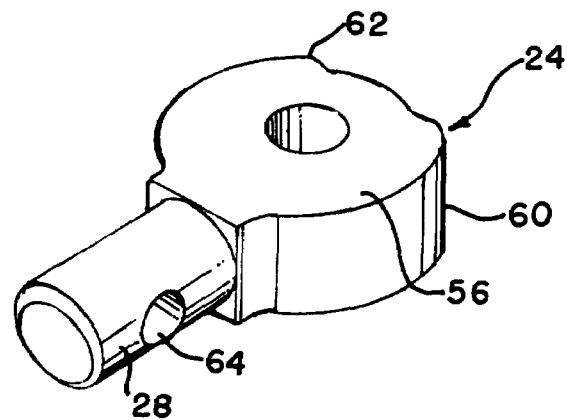
FIG. 4 is a top perspective view of a pivot flange of the retractor blade assembly shown in FIG. 1.

FIG. 4 shows the pivot flange 24 apart from the assembly 10 shown in FIG. 1. The pivot flange 24 has an extension 28 which is received in bore 30 of blade attachment boss 32 which connects with the pivot flange 24 as well as with a shoulder 14 of a retractor blade 12 as shown in FIG. 1.

The connection 36 is in the form of a post with a bore 40 extending therethrough as shown in FIG. 1.

Figure 3:
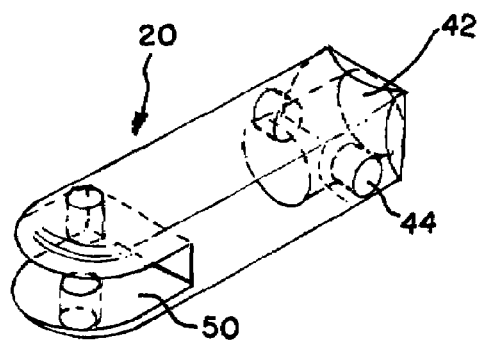
FIG. 3 is a top perspective view of a flange clevis of the retractor blade assembly shown in FIG. 1.

The distal end 38 of the shaft 16 is illustrated in FIG. 1 is inserted into receiver 42 shown in phantom in FIG. 3. Pin 22 shown in FIG. 1 extends through a hole 44 and bore 40 of the connector 36 to retain the shaft 16 relative to the flange clevis 20 as shown in FIG. 1. It is anticipated that this will be a rigid and non-moveable connection, however, in alternative embodiments, this may not necessarily be the case.

FIG. 3 shows the flange clevis 20 having a slot 50 which receives hub 56 of pivot flange 24 shown in FIG. 4. The hub may have a circular circumference or, as illustrated in FIG. 4, may be configured with stops 60,62 which when installed in the slot 50 as shown in FIG. 1, cooperate with the slot 50 to prevent rotation of the hub 56 of more than about 60 degrees to the left or right of shaft axis 17 about rotation axis 60. In other embodiments, the slot 50 may work to restrict the angular movement of the hub 56 independent of stops 60,62 on a hub or other structure. In other embodiments, the hub 56 may be constructed so that 90 degrees or more to the left and right of the shaft axis 17 may be allowed. Pin 26 retains the hub 56 in the slot 50 as shown in FIG. 1 while allowing the hub 56 to pivot. Other connections like a ball and socket joint may be utilized to accomplish this retention and movement capability. It should be understood that the term "pin" is a generic term and can be utilized to mean screw, post or other connection device.

The extension 28 of the pivot flange 24 is received within the bore 30 of the blade attachment boss 32 as shown in FIG. 1. A pin 68 extends through bore 64 in the extension as well as through side slots 66 which not only accommodates the pin 68, but also allows for pivoting about tilting axis 70, at least to a limited degree such as less than about plus or minus twenty degrees relative to shaft axis 17. Tilting axis 70 is preferably perpendicular to as well as spaced from rotation axis 60.

The shoulder 14 of the blade 12 is captured within the mouth 72 of the balde attachment boss 32 and, depending on the tolerances of the shoulder 14 relative to the mouth 72, a connector pin 74 may assist in retaining the shoulder 74 in the mouth 72.

While the clamp 48 is substantially illustrated as a box in FIG. 6, it could have sufficient more structure as shown in co-pending U.S. patent application Ser. No. 10/133,663 or other clamp configurations which show how the retractor shaft 16 can be configured to rotate relative to ring 46 about axes 52,54. The pivoting of a retractor shaft 16 into an incision to direct a retractor blade 12 into a wound has been done, however, the retractor blade has been traditionally rigidly connected to the retractor shaft 16 in the prior art.

Accordingly, as the clamp 48 rotates the retractor shaft 16 downwardly, the tissue contact surface 76 shown in FIG. 1 would be angled at a similar angle as the downward tilt of the retractor shaft 16 relative to the ring 16 at the clamp about the axis 52 in a prior art retractor. Accordingly, the connector 18 allows for the tissue contact surface 76 to be maintained adjacent to tissue 58 (and perpendicular to the direction of retraction) as shown in FIG. 6, even when the retractor shaft 16 is downwardly rotated about axis 52.

Figure 5:
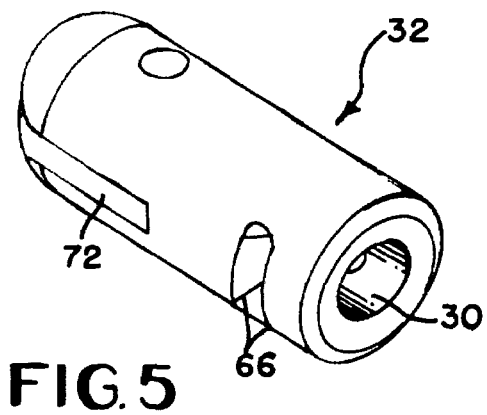
FIG. 5 is a side perspective view of a blade attachment boss of the retractor blade assembly shown in FIG. 1.

Additionally, when the clamp 48 rotates about axis 54 relative to the ring 46 and/or the clamp 48 is positioned so that the plane extending through axis 54 and retractor shaft 16 does not intersect a plane perpendicular to the tissue contact surface 76 extending through stem 14, the tissue contact surface 76 may be still maintained contact with the tissue 58 since the slot 50 allows for the side to side rotation, pivoting or swiveling of the hub 56 about the rotation axis 60, and thus the stem 14 and tissue contact surface 56 of the retractor blade 12 so that it maintains optimal contact with tissue 58 as shown in FIG. 5.

In the preferred embodiment, the hub 56 is free to pivot about rotation axis 60 as necessary within slot 50, however in other embodiments, the slot 50 may be configured to lock the hub 56 in a desired position, if necessary. The pin 68 is also free to move within side slots 66 in the preferred embodiment to allow up and down movement about tilting axis.

Rings 46 known in the art are not necessarily circular in their circumference, and some rings may then be substantially linear. Furthermore, there are a plurality of different kinds of clamps 48 apart from those described and illustrated in co-pending application Ser. No. 10/113,663 which could utilize the assembly 10 shown and described herein.

Although most retractor shafts 16 have a square cross section along a linear length, other cross sectional shapes could also be utilized in accordance with the present invention. Furthermore, depending on a particular anticipated uses and angular relationship of the shoulder 14 relative to retractor shaft 16, the angular travel both laterally (i.e., from side to side as well as top to bottom) may be adjusted. This is believed to assist in maintaining the tissue contact surface 56 in an incision against tissue 58. While the preferred top to bottom range of motion is less than +/−30° and more particularly about +/−20 degrees, and the preferred range of side to side motion is about 120°, these angles may be restricted and/or expanded depending on the particular needs of the retractor system and assembly 10 utilized.

Numerous alterations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

What is claimed is:

1. A retractor assembly comprising:
 a support;
 a clamp selectively positionable at a desired location on the support;
 a retractor shaft connected to the clamp extending away from the clamp and support, and having an end with a shaft axis extending through the end of the retractor shaft, said shaft having a shaft plane extending vertically through said shaft axis;
 a connector connected to the retractor shaft at the end of the retractor shaft and spaced by the retractor shaft from the clamp and support by a length along the shaft axis; and
 a retractor blade connected to the connector, said retractor blade being angularly positionable about the shaft axis in a plane of a tilting axis, said plane of said tilting axis in which said retractor blade angularly rotates being perpendicular to the shaft plane.

2. The retractor assembly of claim 1 wherein the connector allows pivoting of the retractor blade side to side about a rotation axis intermediate a range of about +/−60 degrees relative to the shaft axis.

3. The retractor assembly of claim 1 wherein the tilting axis is spaced from and perpendicular to the rotation axis.

4. The retractor assembly of claim 1 further comprising stops in the connector to limit the angular movement of the retractor blade.

5. The retractor assembly of claim 1 wherein the support is a retractor support ring.

6. The retractor assembly of claim 1 wherein the retractor shaft is substantially linear and extends along the axis.

7. The retractor assembly of claim 1 wherein the connector further comprises a flange clevis connected to the retractor shaft which receives a pivot flange connected to the stem of the retractor blade, and said pivot flange is pivotable about a rotation axis, said rotation axis perpendicularly oriented to the shaft axis and tilting axis.

8. The retractor assembly of claim 7 further comprising a blade attachment boss and the pivot flange is connected to the blade attachment boss which connects to the stem to the retractor blade.

9. The retractor assembly of claim 8 wherein further comprising side slots in the blade attachment boss and the blade attachment boss is connected by a pin restrained by the side slots.

* * * * *